United States Patent
Sembo

(10) Patent No.: US 8,114,897 B2
(45) Date of Patent: Feb. 14, 2012

(54) PESTICIDAL COMPOSITION AND METHOD FOR CONTROLLING A PEST

(75) Inventor: Satoshi Sembo, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 360 days.

(21) Appl. No.: 12/527,766

(22) PCT Filed: Feb. 20, 2008

(86) PCT No.: PCT/JP2008/053347
§ 371 (c)(1),
(2), (4) Date: Aug. 19, 2009

(87) PCT Pub. No.: WO2008/108235
PCT Pub. Date: Sep. 12, 2008

(65) Prior Publication Data
US 2010/0016384 A1    Jan. 21, 2010

(30) Foreign Application Priority Data
Feb. 21, 2007  (JP) .................. 2007-040492

(51) Int. Cl.
*A01N 43/78* (2006.01)
*A01N 53/06* (2006.01)
*A01P 7/04* (2006.01)
(52) U.S. Cl. ........................ 514/365; 514/521
(58) Field of Classification Search .......... 514/365, 514/521
See application file for complete search history.

(56) References Cited

U.S. PATENT DOCUMENTS

| 5,034,404 | A | 7/1991 | Uneme et al. |
| 6,908,945 | B2 | 6/2005 | Mori |
| 7,217,682 | B2 * | 5/2007 | Mori .............................. 504/309 |

FOREIGN PATENT DOCUMENTS

| JP | 3-157308 A | 7/1991 |
| JP | 2004-2363 A | 1/2004 |
| WO | WO-2005/070210 A | 8/2005 |

* cited by examiner

*Primary Examiner* — John Pak
(74) *Attorney, Agent, or Firm* — Birch, Stewart, Kolasch & Birch, LLP

(57) ABSTRACT

A pesticidal composition containing 4-methoxymethyl-2,3,5,6-tetrafluorobenzyl 3-(2-cyano-1-propenyl)-2,2-dimethylcyclopropanecarboxylate and 1-(2-chloro-1,3-thiazolyl)methyl-3-methyl-2-nitroguanidine has a high pesticidal activity.

4 Claims, No Drawings

PESTICIDAL COMPOSITION AND METHOD FOR CONTROLLING A PEST

This application is a 371 of PCT/JP2008/053347, filed on Feb. 20, 2008.

FIELD OF THE INVENTION

The present invention relates to a pesticidal composition and a method for controlling a pest.

DESCRIPTION OF THE RELATED ART 1-(2-Chloro-1,3-thiazolyl)methyl-3-methyl-2-nitroguanidine has been known and used practically as an active ingredient of pesticides (see, for example, JP 3-157308 A).

4-Methoxymethyl-2,3,5,6-tetrafluorobenzyl 3-(2-cyano-1-propenyl)-2,2-dimethylcyclopropanecarboxylate has been known as an active ingredient of pesticides and also to be used together with one or more other pesticides (see, for example, JP 2004-2363 A).

However, 4-methoxymethyl-2,3,5,6-tetrafluorobenzyl 3-(2-cyano-1-propenyl)-2,2-dimethylcyclopropanecarboxylate does not always exhibit a sufficiently satisfactory pesticidal action, when used with another active ingredient of pesticide.

PROBLEMS TO BE SOLVED BY THE INVENTION

An object of the present invention is to provide a pesticidal composition containing 4-methoxymethyl-2,3,5,6-tetrafluorobenzyl 3-(2-cyano-1-propenyl)-2,2-dimethylcyclopropanecarboxylate and having a superior pesticidal activity.

Means for Solving the Problems

After intensive studies to obtain a pesticidal composition containing 4-methoxymethyl-2,3,5,6-tetrafluorobenzyl 3-(2-cyano-1-propenyl)-2,2-dimethylcyclopropanecarboxylate and having a superior insecticidal activity, the inventors have found that a pesticidal composition containing 4-methoxymethyl-2,3,5,6-tetrafluorobenzyl 3-(2-cyano-1-propenyl)-2,2-dimethylcyclopropanecarboxylate (hereinafter referred to as inventive ester compound) and 1-(2-chloro-1,3-thiazolyl)methyl-3-methyl-2-nitroguanidine (hereinafter referred to as inventive guanidine compound) had a superior insecticidal activity, and completed the present invention.

The present invention includes the following aspects:

1. A pesticidal composition comprising the inventive guanidine compound and the inventive ester compound as active ingredients;
2. The composition of 1 above, which has a content ratio of the inventive guanidine compound to the inventive ester compound of from 9:1 to 1:9 in weight basis;
3. A method for controlling a pest, which comprises applying a pesticidal composition containing the inventive guanidine compound and the inventive ester compound as active ingredients to the pest or a place where the pest lives; and
4. The method according to 3 above, wherein the pesticidal composition has a content ratio of the inventive guanidine compound to the inventive ester compound of from 9:1 to 1:9 in weight basis.

Advantages of the Invention

The pesticidal composition according to the present invention exhibits a synergistic effect of these compounds, and thus, is effective in its pesticidal action, even when the concentration of each ingredient is made smaller than that needed when a single ingredient is used or when it is used with the active ingredient of another pesticide.

DESCRIPTION OF THE PREFERRED EMBODIMENTS

The pest-controlling composition according to the present invention is characterized by containing the inventive guanidine compound and the inventive ester compound.

The inventive guanidine compound is a compound described in JP 3-157308 A and can be prepared by the method described therein. The inventive guanidine compound has isomers, based on the double bond in the nitro imino group; however, these isomers may be contained at any ratio in the composition according to the present invention.

A commercial product available under a general name of clothianidin may be used as the inventive guanidine compound.

The inventive ester compound is a compound described, for example, in JP 2004-2363 A and can be prepared by the method described therein.

The inventive ester compound has isomers, based on its two asymmetric carbons in the cyclopropane ring and also on a carbon-carbon double bond; however, the active isomers may also be contained at any ratio in the composition according to the present invention.

Examples of the pests against which the pesticidal composition according to the present invention is effective include pest arthropods such as pest insects, pest mites, and the like, and specific examples thereof include the followings:

Lepidoptera

Pyralidae (pyralid moths) such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae (tortricid moths) such as *Adoxophyes* spp.; Carposinidae; Lyonetiidae (lyonetiid moths); Lymantriidae (tussock moths); *Antographa* spp.; *Agrotis* spp. such as *Agrotis segetum* (turnip cutworm) and *Agrotis ipsilon* (black cutworm); *Helicoverpa* spp.; *Heliothis* spp.; *Plutella xylostella* (diamondback moth); *Parnara guttata* (rice skipper); *Tinea pellionella* (casemaking clothes moth); *Tineola bisselliella* (webbing clothes moth); etc.

Diptera

*Culex* spp. such as *Culex pipiens pallens* (common mosquito) and *Culex tritaeniorhynchus*; *Aedes* spp. such as *Aedes aegypti* and *Aedes albopictus*; *Anopheles* spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae (anthomylid flies) such as *Delia platura* (seedcorn maggot) and *Delia antiqua* (onion maggot); Tephritidae (fruit flies); Drosophilidae (small fruit flies, vinegar flies); Psychodidae (moth flies, sand flies); Phoridae; Simuliidae (black flies); Tabanidae; Stomoxyidae (stable flies); biting midges; etc.

Dictyoptera

*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach), etc.

*Hymenoptera*

Formicidae (ants); Vespidae (hornets); Bethylidae (bethylid wasps); Tenthredinidae (sawflies) such as *Athalia rosae ruficornis* (cabbage sawfly); etc.

*Siphonaptera*

*Ctenocephalides canis, Ctenocephalides felis, Pulex irritans*, etc,

Anoplura

*Pediculus humanus, Phthirus pubis, Pediculus humanus* var. *capitis, Pediculus humanus* var. *corporis*, etc.

*Isoptera*(termites)

*Reticulitermes speratus, Coptotermes formosanus* (Formosan subterranean termite), etc.

Hemiptera

Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leaf-hoppers) such as *Nephotettix cincticeps* (green rice leafhopper) and *Nephotetti virescens* (green rice leafhopper); Aphididae (aphids); Pentatomidae (bugs); Aleyrodidae (whiteflies); Coccidae (scales); Tingidae (lace bugs); Psyllidae (psyllids); etc.

Coleoptera

*Attagenus unicolor; Anthrenus verbasci* (varied carpet beetle); corn rootworms such as *Diabrotica virgifera* (western corn rootworm) and *Diabrotica undecimpunctaca howardi* (southern corn rootworm); Scarabaeidae (scarabs) such as *Anomala cuprea* (cupreous chafer) and *Anomala rufocuprea* (soybean beetle); Curculionidae (weevils) such as *Sitophilus zeamais* (maize weevil), *Lissorhoptrus oryzophilus* (ricewater weevil), *Anthonomus grandis grandis* (boll weevil) and *Callosobruchus chinensis* (adzuki bean weevil); Tenebrionidae (darkling beetles) such as *Tenebrio molitor* (yellow mealworm) and *Tribolium castaneum* (red fluor beetle); *Chrysomelidae* (corn rootworms) such as *Oulema oryzae* (rice leaf beetle), *Phyllotreta striolata* (striped flea beetles) and *Aulacophora femoralis* (cucurbit leaf beetle); Anobiidae; *Epilachna* spp. such as *Henosepilachna vigintioctopunctata* (twenty-eight-spotted ladybirds); Lyctidae (powder post beetles); Bostrychidae (false powder post beetles); Cerambycidae; *Paederus fuscipes* (robe beetle); etc.

Thysanoptera (thrips)

*Thrips palmi, Franklinella occidentalis* (western flower thrips), *Thrips hawaiiensis* (flower thrips), etc.

Orthoptera

Gryllotalpidae (mole crickets), Acrididae (grasshoppers), etc.

Acarina (Mites and Ticks)

Pyroglyphidae such as *Dermatophagoides farinae* and *Dermatophagoides pteronyssinus*; Acaridae such as *Tyrophagus putrescentiae* Schrank (mold mite, copra mite, forage mite) and *Aleuroglyphus ovatus* Troupeau (brown legged grain mite); Glycyphagidae such as *Glycyphagus privatus, Glycyphagus domesticus* and *Glycyphagus destructor* Schrank (groceries mite); Cheyletidae such as *Cheyletus melaccensis* and *Cheyletus moorei*; Tarsonemidae; Chrtoglyphus; Oribatei; Tetranychidae (spider mites) such as *Tetranychus urticae* (two-spotted spider mite), *Tetranychus kanzawai* (Kanzawa spider mite), *Panonychus citri* (citrus red mite) and *Panonychus ulmi* (European red mite); Ixodidae such as *Haemaphysalis loncricornis*; etc.

The content ratio of the inventive guanidine compound to the inventive ester compound contained in the pesticidal composition according to the present invention is normally from 30:1 to 1:20, preferably from 9:1 to 1:9, and more preferably from 9:1 to 1:3 in weight basis.

The inventive guanidine and ester compounds may be used in the pesticidal composition according to the present invention as a mixture, but they are normally used in the form of formulations. The formulations include, for example, oil formulations, emulsifiable concentrates, wettable powders, flowable concentrates such as aqueous suspension concentrates, aqueous emulsion concentrates, etc., granules, dusts, aerosols, heat vaporization formulations (insecticide coil, insect electrocuting mat, heated insecticide-vaporizing agent with liquid-absorptive wick, etc.), heated fumigants (self-combustion fumigant, chemical-reaction fumigant, porous-ceramic-plate fumigant, etc.), unheated vaporization formulations (resin vaporization agent, impregnated paper vaporization agent, etc.), spraying agents (fogging, etc.), ULV preparations, and poisonous baits.

These formulations are produced, for example, by the following methods:

(1) Method of mixing the inventive guanidine and ester compounds with a solid carrier, liquid carrier, gas carrier, bait, or the like, and additionally other auxiliaries for formulation such as surfactant if needed, and processing the mixture;

(2) Method of impregnating a base material containing no active ingredient with the inventive guanidine and ester compounds; and (3) Method of mixing the inventive guanidine and ester compounds with a base material and molding the mixture.

The inventive guanidine and ester compounds are normally contained in a total amount of 0.01 to 90 wt % in these formulations, although the content varies depending on the form of the formulation.

Examples of the solid carriers used for formulation include clays (e.g., kaolin clay, diatomaceous earth, synthetic hydrated silicon oxide, bentonite, Fubasami clay, acid clay, etc.), talcs, ceramics, other inorganic minerals (e.g., sericite, quartz, sulfur, activated carbon, calcium carbonate, hydrated silica, montmorillonite, etc.), chemical fertilizers (e.g., ammonium sulfate, ammonium phosphate, ammonium nitrate, urea, ammonium chloride, etc.) and the like. Examples of the liquid carriers include water, alcohols (e.g., methanol, ethanol, etc.), ketones (acetone, methyl ethyl ketone, etc.), aromatic hydrocarbons (e.g., benzene, toluene, xylene, ethylbenzene, methylnaphthalene, phenylxylylethane, etc.), aliphatic hydrocarbons (e.g., hexane, cyclohexane, kerosene, light oil, etc.), esters (e.g., ethyl acetate, butyl acetate, etc.), nitrites (e.g., acetonitrile, isobutyronitrile, etc.), ethers (diisopropylether, dioxane, etc.), acid amides (e.g., N,N-dimethylformamide, N,N-dimethylacetamide, etc.), halogenated hydrocarbons (e.g., dichloromethane, trichloroethane, carbon tetrachloride, etc.), dimethylsulfoxide, vegetable oils (e.g., soy bean oil, cottonseed oil, etc.) and the like. Examples of the gaseous carriers include CFC gases, butane gas, LPG (liquefied petroleum gas), dimethyl ether, carbon dioxide gas, and the like.

The surfactant includes, for example, alkyl sulfate salts, alkylsulfonates, alkylarylsulfonates, alkyl aryl ethers and their polyoxyethylenated products, polyethylene glycol ethers, polyhydric alcohol esters and sugar alcohol derivatives.

Other auxiliaries for formulation include adhesive agent, dispersants, stabilizers, and others, and specific examples thereof include casein, gelatin, polysaccharides (e.g., starch powder, gum arabic, cellulose derivatives, alginic acid, etc.), lignin derivatives, bentonite, saccharides, synthetic water-soluble polymers (polyvinyl alcohols, polyvinylpyrrolidones), polyacrylic acid, BHT (2,6-di-tert-butyl-4-methylphenol), and BHA (a mixture of 2-tert-butyl-4-methoxyphenol and 3-tert-butyl-4-methoxyphenol).

The base material of the insecticide coil is, for example, a mixture of a vegetable powder such as wood powder or sake lees powder and a binder such as tabu powder (powdered leaves of the *Machilus thunbergii* tree), starch, or gluten.

The base material for the insect electrocuting mat is, for example, a cotton linter molded into the plate shape, or a molding of a mixed fibril of cotton linter and pulp in the plate shape.

Examples of the base materials for the self-combustion pesticide include combustible heat-generating agents such as nitrate salts, nitrite salts, guanidine salts, potassium chlorate, nitrocellulose, ethylcellulose, and wood powder; thermal decomposition stimulants such as alkali-metal salts, alkali-earth metal salts, dichromate salts, and chromate salts; oxygen-supplying agents such as potassium nitrate; combustion aides such as melamine and wheat starch; extenders such as diatomaceous earth; and binders such as synthetic adhesives.

Examples of the base materials for the chemical-reaction fumigant include heat-generating agents such as alkali metal sulfides, polysulfides, and hydrosulfides and calcium oxide; catalysts such as carbonaceous substances, iron carbide, and activated clay; organic foaming agents such as azo dicarbonamide, benzenesulfonyl hydrazide, dinitropentamethylenetetramine, polystyrene, and polyurethane; fillers such as natural and synthetic fibrils; and the like.

Examples of the base materials for the unheated vaporization formulation include thermoplastic resins and papers (filter paper, Japanese paper, etc.).

Examples of the base materials for the poisonous bait include feedstuff components such as vegetable powder, vegetable oil, saccharides, and crystalline cellulose; antioxidants such as dibutylhydroxytoluene and nordihydroguaiaretic acid; preservatives such as dehydroacetic acid; stimulants for prevention of unintended intake by children or pets such as red pepper powder; insect-attracting flavors such as of cheese, onion, and peanut oil.

The method for controlling a pest according to the present invention is practiced by applying the pesticidal composition according to the present invention to the pest or a place where the pest lives.

The method of applying the pesticidal composition according to the present invention includes specifically the following methods, and is selected properly according to the form, the use site and others of the pesticidal composition according to the present invention.

(1) Method of applying the pesticidal composition according to the present invention to the pest or a place where the pest lives as it is.

(2) Method of diluting the pesticidal composition according to the present invention with a solvent such as water and then applying the diluted mixture to the pest or a place where the pest lives.

In this case, normally, the pesticidal composition according to the present invention, which is contained in a formulation such as emulsifiable concentrates, wettable powders, flowable concentrates, or microcapsular formulation, is diluted to a total concentration of the inventive guanidine and ester compounds at 0.1 to 10,000 ppm.

(3) Method of heating the pesticidal composition according to the present invention to vaporize the active ingredients therein at the place where the pest lives.

In this case, the dosage and the dosage concentration of the inventive guanidine and ester compounds are determined properly according to the form, application period, application site, and application method of the pesticidal composition according to the present invention and also to the kind of the pest, the damage by the pest, and other factors.

The pesticidal composition according to the present invention may be used as mixed or in combination with other materials such as another insecticide, nematicide, soil pesticide, bactericide, herbicide, plant growth regulator, repellent, synergist, fertilizer, and soil-improving agent.

Examples of the active ingredients in the insecticides and acaricides include:

organic phosphorus compounds such as Fenitrothion, Fenthion, Diazinon, chlorpyrifos, Acephate, Methidathion, Disulfoton, DDVP, Sulprofos, Cyanophos, Dioxabenzophos, Demethoate, Phenthoate, Malathion, Trichlorfon, Azinphosmethyl, Monocrotophos, and Ethion; carbamate compounds such as BPMC, Benfuracarb, Propoxur, Carbosulfan, Carbaryl, Methomyl, Ethiofencarb, Aldicarb, Oxamyl, and Fenothiocarb; pyrethroid compounds such as Etofenprox, Fenvalerate, Esfenvalerate, Fenpropathrin, Cypermethrin, Permethrin, Cyhalothrin, Deltamethrin, Cycloprothrin, Fluvalinate, Bifenthrin, 2-methyl-2-(4-bromodifluoromethoxyphenyl)propyl(3-phenoxybenzyl)ether, Tralomethrin, Silafluofen, d-Phenothrin, Cyphenothrin, d-Resmethrin, Acrinathrin, Cyfluthrin, Tefluthrin, Transfluthrin, Tetramethrin, Allethrin, d-Furamethrin, Prallethrin, Empenthrin, 5-(2-propynyl)furfuryl 2,2,3,3-tetramethylcyclopropanecarboxylate;

chlorinated hydrocarbon compounds such as Endosulfan, γ-BHC, and 1,1-bis(chlorophenyl)-2,2,2-trichloroethanol;

benzoylphenyl urea compounds such as Chlorfluazuron, Teflubenzuron, and Fulfenoxlon;

phenylpyrazole compounds, Metoxadiazone, Bromopropylate, Tetradifon, Chinomethionate, Pyridaben, Fenpyroximate, Diafenthiuron, Tebufenpyrad, Polynactin complexes [tetranactin, dinactin and trinactin], Pyrimidifen, Milbemectin, Abamectin, Ivermectin, Azadirachtin, and the like.

The repellents include, for example, 3,4-caranediol, N,N-diethyl-m-toluamide, 1-methylpropyl 2-(2-hydroxyethyl)-1-piperidinecarboxylate, p-menthane-3,8-diol, and plant essential oils such as hyssop oil.

Examples of the synergists include bis-(2,3,3,3-tetrachloropropyl)ether [S-421], N-(2-ethylhexyl)bicyclo[2,2,1]hept-5-ene-2,3-dicarboxylmide [MGK-264], and α-[2-(2-butoxyethoxy)ethoxy]-4,5-methylenedioxy-2-propyltoluene [piperonyl butoxide].

EXAMPLES

Hereinafter, the present invention will be described in more detail with reference to Formulation Examples and Examples, but it should be understood that the present invention is not restricted thereby.

First, Formulation Examples of the pesticidal composition according to the present invention will be described.

Formulation Example 1

Five parts of the inventive ester compound and 10 parts of the inventive guanidine compound are dissolved in 70 parts of xylene, and 15 parts of Solpole 3005X® (Toho Chemical Industry) is added and mixed thoroughly therein, to give an emulsifiable concentrate.

Formulation Example 2

Five parts of Solpole 3005X is added to 10 parts of the inventive ester compound and 30 parts of the inventive guanidine compound; the mixture is stirred thoroughly; 32 parts of Carplex® #80 (synthetic hydrated silicon oxide, Shionogi &

Co., Ltd.) and 23 parts of 300-mesh diatomaceous earth are added thereto; and the mixture is blended in a juice mixer, to give a wettable powder.

Formulation Example 3

0.5 part of the inventive ester compound, 1 part of the inventive guanidine compound, 1 part of Tokuseal GUN (synthetic hydrated silicon oxide, manufactured by Tokuyama Corp.), 2 parts of Reax 85 A (sodium ligninsulfonate, manufactured by Westvaco chemicals) 30 parts of Bentonite Fuji (bentonite, manufactured by Hojun Co., Ltd.) and 65.5 parts of Shokozan A Clay (kaolin clay, manufactured by Shokozan Kogyosho) are mixed and pulverized; water is added thereto; and the mixture is milled thoroughly, granulated in an extruding granulator, and dried, to give a granule.

Formulation Example 4

Two parts of the inventive ester compound, 8 parts of the inventive guanidine compound, 10 parts of phenylxylylethane and 0.5 part of Sumidur L-75 (tolylene diisocyanate, manufactured by Sumitomo Bayer Urethane Co., Ltd.) are mixed; the mixture is added to 20 parts of 10% aqueous gum arabic solution; the mixture is agitated in a homomixer, to give an emulsion containing particles having an average diameter of 20 μm. Two parts of ethylene glycol is added thereto, and the mixture is stirred in a hot bath at 60° C. for 24 hours, to give a microcapsule slurry. Separately, 0.2 part of xanthan gum and 1.0 part of Veegum R (aluminum magnesium silicate, manufactured by Sanyo Chemical Industries, Ltd.) are dispersed in 56.3 parts of ion-exchange water, to give a thickener solution. 42.5 Parts of the microcapsule slurry above and 57.5 parts of the thickener solution are mixed, to give a microcapsule.

Formulation Example 5

Three parts of the inventive ester compound, 7 parts of the inventive guanidine compound and 10 parts of phenylxylylethane are mixed; the mixture is added to 20 parts of 10% aqueous polyethylene glycol solution; and the mixture is agitated in a homomixer, to give an emulsion containing particles having an average diameter of 3 μm. Separately, 0.2 part of xanthan gum and 1.0 part of Veegum R (aluminum magnesium silicate, manufactured by Sanyo Chemical Industries, Ltd.) are dispersed in 58.8 parts of ion-exchange water, to give a thickener solution. Forty parts of the emulsion solution and 60 parts of the thickener solution are mixed, to give a flowable agent.

Formulation Example 6

Two parts of the inventive ester compound and 4 parts of the inventive guanidine compound are added to 3 parts of Carplex® #80 (synthetic hydrated silicon oxide, Shionogi & Co., Ltd.), 0.3 part of PAP (mixture of monoisopropyl phosphate and diisopropyl phosphate) and 90.7 parts of talc (300 mesh); and the mixture is blended in a juice mixer, to give a dust.

Formulation Example 7

0.05 part of the inventive ester compound and 0.15 part of the inventive guanidine compound are dissolved in 10 parts of dichloromethane, and the mixture is mixed with 89.8 parts of deodorized kerosene, to give an oil formulation.

Formulation Example 8

0.1 part of the inventive ester compound, 0.9 part of the inventive guanidine compound, 5 parts of dichloromethane and 34 parts of deodorized kerosene are mixed and dissolved; the mixture is filled in an aerosol container; after connection of a valve, 60 parts of a propellant (liquefied petroleum gas) is fed therein through the valve under pressure, to give an oil-based aerosol.

Formulation Example 9

0.2 part of the inventive ester compound, 0.4 part of the inventive guanidine compound, 5 parts of xylene, 3.4 parts of deodorized kerosene and 1 part of Atmos® 300 (emulsifier, Atlas chemical Co.) are mixed and dissolved; and the mixture and 50 parts of water are filled in an aerosol container; 40 parts of a propellant (liquefied petroleum gas) is fed therein through a valve under pressure, to give an aqueous aerosol.

Formulation Example 10

40 mg of the inventive ester compound and 60 mg of the inventive guanidine compound are dissolved in a suitable amount of acetone; a porous ceramic plate of 4 cm×4 cm in size and 1.2 cm in thickness was impregnated with the solution, to give a heat fumigant.

Hereinafter, the beneficial effectiveness of the pesticidal composition according to the present invention in controlling pests will be described with reference to Test Example.

Test Example

Suitable amounts of 4-methoxymethyl-2,3,5,6-tetrafluorobenzyl(1R)-trans-3-(2-cyano-1-propenyl)-2,2-dimethyl-cyclopropanecarboxylate (isomer ratio, based on double bond, Z/E: approximately 2/1) (hereinafter, referred to as compound A) and/or clothianidin (manufactured by Sumika Takeda Agrochemicals Co.) are mixed with diethylene glycol monomethylether, to give a test formulation solution containing the compound A and/or clothianidin at particular concentrations (see Table 1).

A triangular prism wooden container (regular triangle having a base of 3.5 cm and a height of 15 cm) containing 10 cockroaches *Blattella germanica* (5 males and 5 females) hidden therein was placed in the bottom center of a cubic glass box having a base of 70 cm square. 4.2 Milliliters of the test formulation solution was sprayed on the glass box with a spray gun. In 10 minutes after the spraying, the cockroaches were transferred into a plastic container containing food and water and left there for 3 days. The number of live cockroaches was then counted, to give a mortality rate. The test was repeated in duplicate, and the average thus obtained is shown in Table 1.

TABLE 1

| | Ingredient concentration (% (W/V)) | | Mortality rate (%) |
|---|---|---|---|
| | Compound A | Clothianidin | |
| 1 | 0.05 | 0.05 | 100 |
| 2 | 0.02 | 0.18 | 100 |
| 3 | 0.05 | 0.15 | 100 |

TABLE 1-continued

| | Ingredient concentration (% (W/V)) | | Mortality rate (%) |
|---|---|---|---|
| | Compound A | Clothianidin | |
| 4 | 0.1 | 0.1 | 100 |
| 5 | 0.15 | 0.05 | 90 |
| 6 | 0.18 | 0.02 | 55 |
| 7 | 0.2 | — | 5 |
| 8 | — | 0.2 | 35 |

Referential Test Example

Suitable amounts of the compound A and either (E)-$N^1$-[(6-chloro-3-pyridyl)methyl]-$N^2$-cyano-$N^1$-methylacetamidine (general name: acetamiprid, hereinafter, referred to as N-cyanoacetamidine compound) or 1-(6-chloro-3-pyridylmethyl)-N-nitroimidazolidin-2-ylidene amine (general name: imidacloprid, hereinafter referred to as nitroimidazoline compound) are mixed with diethylene glycol monomethylether, to give test formulation solutions containing the compound A and either the N-cyano acetamidine or nitroimidazoline compound at particular concentrations (see Table 2).

A triangular prism wooden container (regular triangle having a base of 3.5 cm and a height of 15 cm) containing 10 cockroaches *Blattella germanica* (5 males and 5 females) hidden therein was placed in the bottom center of a cubic glass box having a base of 70 cm. 4.2 Milliliters of the test formulation solution was sprayed on the glass box with a spray gun. In 10 minutes after the spraying, the cockroaches were transferred into a plastic container containing food and water and left there for 3 days. The number of live cockroaches was then counted, to give a mortality rate. The test was repeated in duplicate, and the average thus obtained is shown in Table 2.

TABLE 2

| | Ingredient concentration (% (w/v)) | | | Mortality rate (%) |
|---|---|---|---|---|
| | Compound A | N-Cyanoacetamide compound | Nitroimidazoline compound | |
| 9 | 0.1 | 0.1 | — | 10 |
| 10 | 0.1 | — | 0.1 | 15 |
| 11 | 0.2 | — | — | 5 |
| 12 | — | 0.2 | — | 5 |
| 13 | — | — | 0.2 | 15 |

The invention claimed is:

1. A pesticidal composition comprising 1-(2-chloro-1,3-thiazolyl)methyl-3-methyl-2-nitroguanidine and 4-methoxymethyl-2,3,5,6-tetrafluorobenzyl 3-(2-cyano-1-propenyl)-2,2-dimethylcyclopropanecarboxylate as active ingredients.

2. The composition according to claim 1, which has a content ratio of 1-(2-chloro-1,3-thiazolyl)methyl-3-methyl-2-nitroguanidine to 4-methoxymethyl-2,3,5,6-tetrafluorobenzyl 3-(2-cyano-1-propenyl)-2,2-dimethylcyclopropanecarboxylate of from 9:1 to 1:9 in weight basis.

3. A method for controlling a pest which comprises applying an effective quantity of a pesticidal composition containing 1-(2-chloro-1,3-thiazolyl)methyl-3-methyl-2-nitroguanidine and 4-methoxymethyl-2,3,5,6-tetrafluorobenzyl 3-(2-cyano-1-propenyl)-2,2-dimethylcyclopropanecarboxylate as active ingredients to the pest or a place where the pest lives.

4. The method according to claim 3, wherein the pesticidal composition has a content ratio of 1-(2-chloro-1,3-thiazolyl)methyl-3-methyl-2-nitroguanidine to 4-methoxymethyl-2,3,5,6-tetrafluorobenzyl 3-(2-cyano-1-propenyl)-2,2-dimethylcyclopropanecarboxylate of from 9:1 to 1:9 in weight basis.

* * * * *